United States Patent [19]

Foti

[11] Patent Number: 4,992,247

[45] Date of Patent: Feb. 12, 1991

[54] CONTAINER STERILIZATION SYSTEM

[75] Inventor: Robert C. Foti, Livonia, Mich.

[73] Assignee: Elopak Systems, A.G., Glattbugg, Switzerland

[21] Appl. No.: 350,160

[22] Filed: May 11, 1989

[51] Int. Cl.⁵ .......................... A61L 2/20; B65B 55/10
[52] U.S. Cl. ...................................... 422/304; 53/425; 53/111 RC; 99/483; 422/28; 422/31; 422/298; 422/302; 426/521
[58] Field of Search ................... 422/28, 31, 304, 298, 422/302; 53/425, 111 RC; 99/483; 426/521

[56] References Cited

U.S. PATENT DOCUMENTS 4,707,334  11/1987  Gerhard ........................... 422/304 X
4,742,667  5/1988   Müller et al. ................... 422/304 X Primary Examiner—Robert J. Warden
Assistant Examiner—Jill Johnston
Attorney, Agent, or Firm—John P. Moran

[57] ABSTRACT

A container sterilization system adaptable to a forming, filling and sealing machine used to process containers for liquids or spoonable food products. The system is a closed loop system including ductwork interconnecting a suitable blower for directing through the closed loop a flow of a mixture of air, vaporized hydrogen peroxide, and vaporized water; a duct heater; one of a vapor generation pool or a vapor generation stack with heat exchanger; a suitable vapor delivery inlet manifold and an associated exhaust manifold; and a drying air inlet manifold and an associated exhaust with containers being conveyed laterally intermediate the inlet manifolds and the exhaust manifolds.

22 Claims, 2 Drawing Sheets

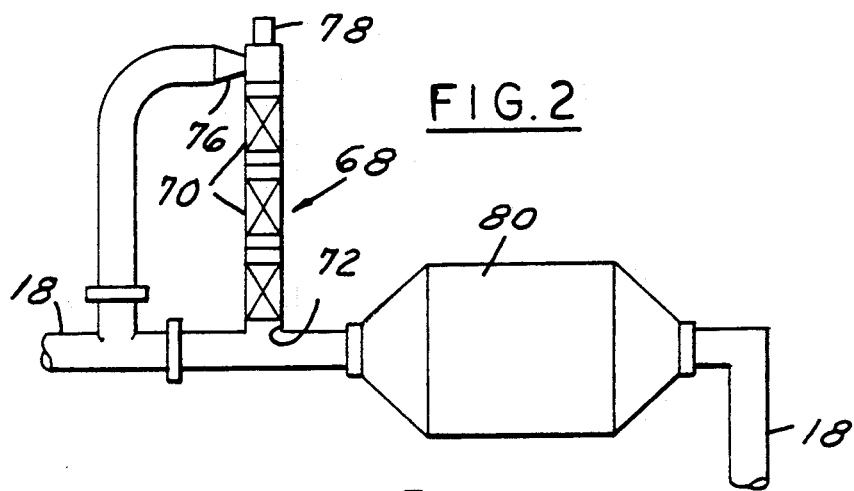
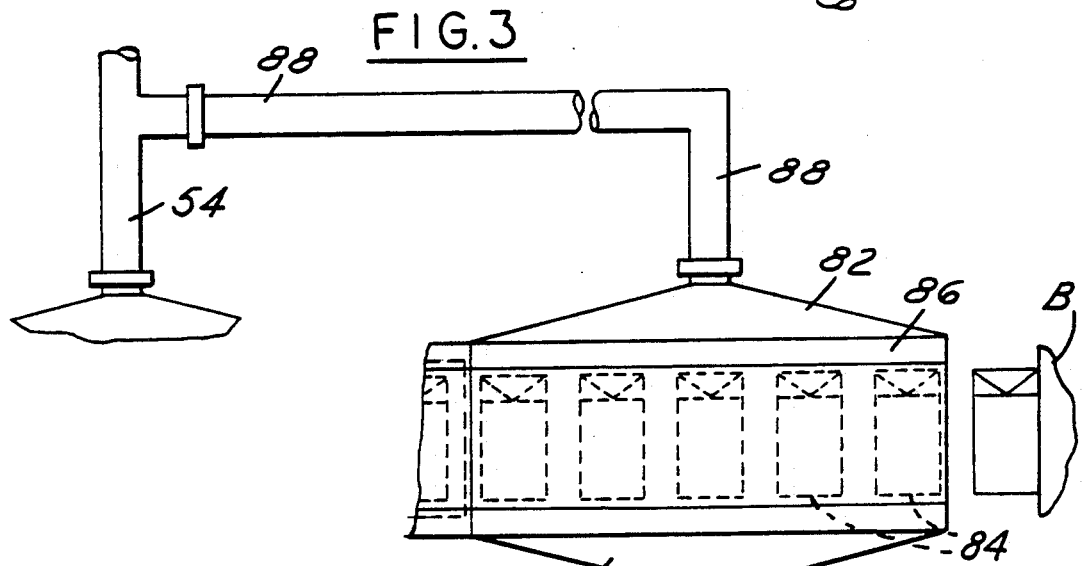
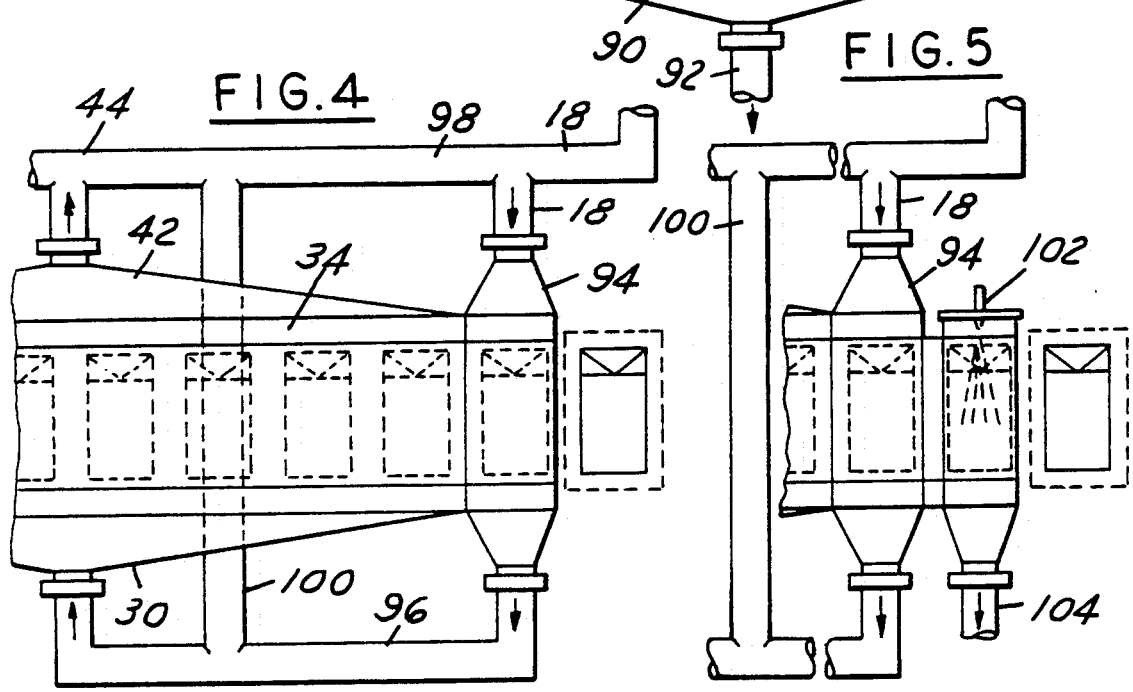

CONTAINER STERILIZATION SYSTEM

TECHNICAL FIELD

This invention relates generally to systems for sterilizing containers such as paperboard cartons for carrying not-carbonated or "still" liquids, such as juices, and, more particularly, to such systems which are closed loop systems which may be operative in conjunction with existing forming, filling and sealing machines.

BACKGROUND ART

Forming, sterilizing, filling and sealing machines have incorporated various techniques heretofore to sterilize paperboard cartons for carrying non-carbonated or "still" liquids, such as juices. One such machine is shown and described in U.S. Pat. No. 3,566,575, wherein a hydrogen peroxide mixture is supplied via an integrally mounted fogging nozzle into the open tops of cartons being fed through the machine, and heated therein to remove the fog from the cartons just prior to being filled with the designated liquid.

Another forming, filling and sealing machine incorporating a sterilization section intermediate the bottom forming and sealing section and the filling and top forming and sealing section is shown and described in U. S. Pat. No. 4,566,251, wherein the sterilization section has a separate conveyor for carrying the cartons through the latter section, and subjecting them to a sterilant vapor at a temperature substantially higher than that of the cartons, causing the vapor to condense on all surfaces of the carton, and then turned upside down by the conveyor to allow any condensate to drain therefrom while being dried prior to being lowered in an upright position.

Insofar as closed loop systems are concerned, for use with a container filling machine through which the containers are conveyed, Sjostraud No. 4,055,035 discloses a method of extracting sterilized air and vapor from a web type packaging machine, passing it through a liquid ring compressor, and returning a purified air to the packaging machine where the web has been subjected to sterilant by an application roller.

DISCLOSURE OF THE INVENTION

A general object of the present invention is to provide an improved closed loop sterilization system which may be adapted to a conventional carton forming, filling and sealing machine wherein a predetermined number of indexing stations, say, fourteen stations, are available between the bottom forming/sealing section and the filling/top forming/sealing section for cooperation with the sterilization system.

Another object of the invention is to provide a closed loop sterilization system including a predetermined solution of hydrogen peroxide processed through cooperating duct heater, heat exchanger, inlet and exhaust manifolds, and either a vapor generation pool or vapor generation stack, in conjunction with a logitudinal chamber extending intermediate the inlet and exhaust manifolds, through which a section of a conveyor of a forming, filling and sealing machine may traverse, conveying cartons enroute to being filled with a liquid or spoonable food product.

These and other objects and advantages will become more apparent when reference is made to the following description and accompanying drawings.

BRIEF DESCRIPTION OF THE DRAWINGS

FIG. 2 is a diagramatic layout of an alternate embodiment of a closed loop sterilization system embodying the invention.

Referring now to the drawings in greater detail, FIG. 1 illustrates a container sterilization system 10 of a closed-loop type, which may be adapted to machines used to process the forming, filling and sealing of containers for liquids and spoonable foods. The system 10 is mounted around a section of the machine intermediate the usual bottom forming and sealing section, represented as B, and the usual top forming, filling and sealing section, represented as T.

Figure 1:
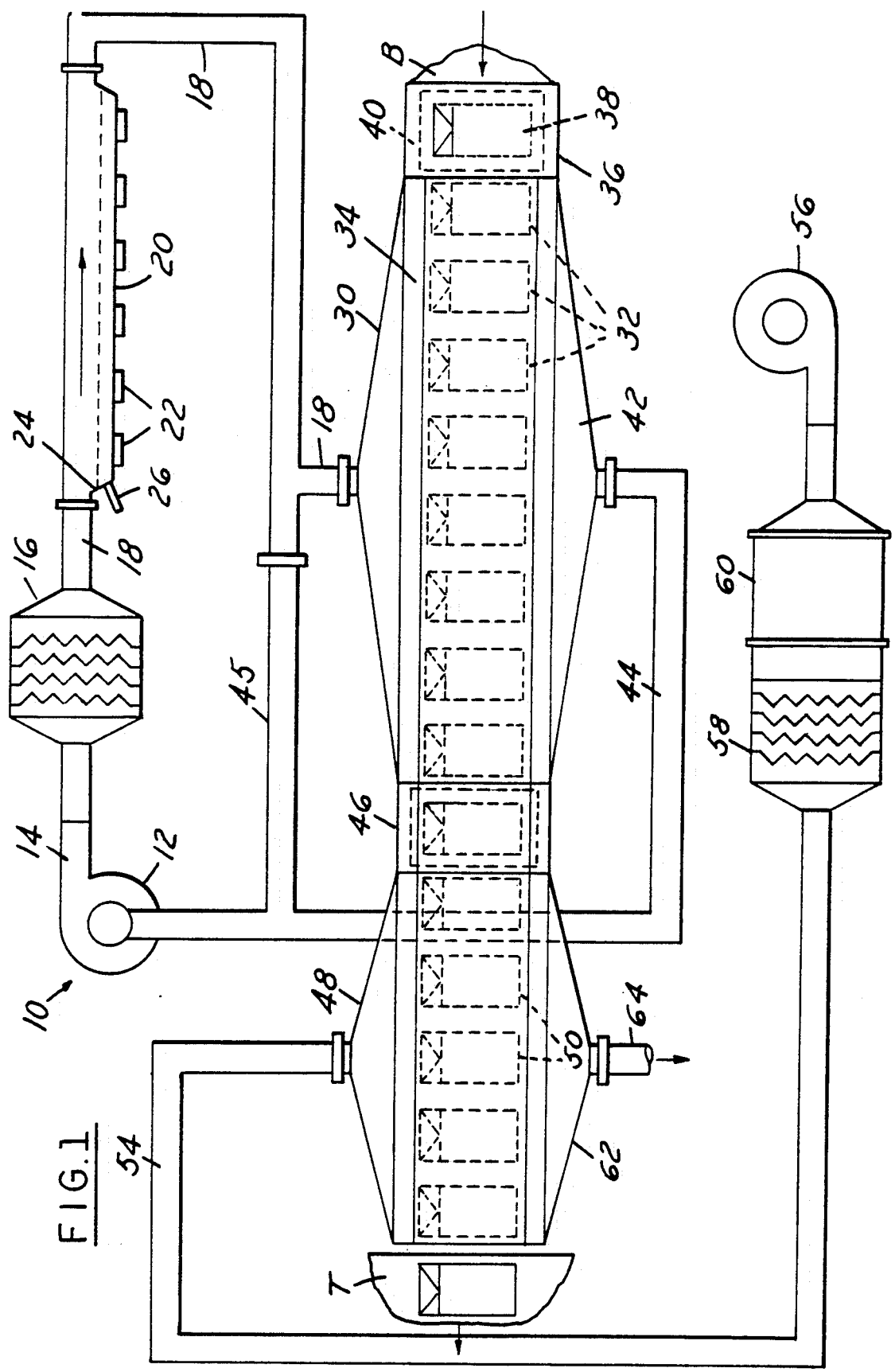
FIG. 1 is a diagramatic layout of a closed loop sterilization system embodying the invention.

The closed-loop system includes a suitable blower unit, such as a Paxton blower 12, available from Paxton Products, Inc., for initially blowing sterile air from its outlet 14 into and through a duct heater 16, which serves to raise the temperature of the air to 200° F. as it enters a first insulated duct 18. The duct 18 leads to a vapor generation pool 20 containing a 35% solution of hydrogen peroxide maintained at 200° F. by a plurality of electric heaters 22. The inner surface of the duct may be coated with Teflon or similar inert material to minimize potential for hydrogen peroxide decomposition. The duct 18 communicates with the liquid surface of the vapor generation pool 20, and serves to allow the density of the hydrogen peroxide in the airstream to equal the density of the hydrogen peroxide at the surface of the vapor generation pool.

Hydrogen peroxide solution, as required, is dispersed into the pool 20. An inlet 26 just adjacent of the electric heaters 22 admits additional hydrogen peroxide into the pool 20 when required.

The resultant air stream in the duct 18 above the cooler 20 now contains vaporized hydrogen peroxide which flows to a vapor delivery inlet manifold 30. The manifold 30 covers eight indexing stations 32 in a chamber 34 through which a suitable conveyor, represented at 36, conveys containers 38. An inlet iso-box or isolation box 40 is mounted at the inlet end of the vapor delivery inlet manifold 30, serving as an air lock or curtain to prevent outside contaminants from entering the chamber 34 and to prevent the vaporized hydrogen peroxide from leaving the chamber.

A vapor delivery return manifold 42 below the chamber 34 communicates with an insulated duct 44 which leads back to the blower 12 for the next cycle. A branch duct 45 communicates between the ducts 18 and 44.

As referenced above, containers 38 are conveyed by the conveyor 36 through the chamber 34. The containers are open-topped and preheated prior to entering the chamber 36 through the inlet iso-box 40. While indexing beneath the manifold 30 the vaporized hydrogen peroxide from the duct 18 condenses onto the inner surfaces of the containers 38 prior to exiting through an outlet which includes another iso-box 46. The rate of mass transfer of hydrogen peroxide solution must exceed the application rate of the solution. This is controlled by the initial pre-heat temperature of the containers.

While being indexed by the conveyor 36 through the chamber 34, the incoming dry, pre-heated containers 38 are subjected to a three-stage process. First, as dry pre-heated cartons enter the condensing stations, the peroxide rich air flows from the manifold 30 and liquid hydrogen peroxide and water condenses in measured amounts on the container. Second, as the container continues through the eight sterilizing stations, equilibrium is achieved between the container, with liquid hydrogen peroxide coverage, and the peroxide rich air, the latter serving to scrub the container. Since the container with hydrogen peroxide coverage is at equilibrium with the peroxide rich air, the container temperatures and hydrogen peroxide coverage is maintained in these stations. The maintenance of this hydrogen peroxide coverage at the process temperatures provides a sterilizing effect for the container.

Adjacent the iso-box 46 is a drying air inlet manifold 48 covering five conveyor indexing stations 50 in a chamber 52, serving to remove the condensate mixture from the containers. The drying air is transmitted to the manifold 48 via a duct 54 leading from a blower 56. A duct heater 58 and a HEPA filter 60 are mounted in the duct 54.

An exhaust manifold 62 below the chamber 52 communicates with an exhaust duct 64.

Referring now to FIG. 2, the vapor generation pool 20 and its associated electric heater 22 and inlet 26 of FIG. 1 are replaced by a vapor generation stack arrangement 66 mounted in the duct 18. The arrangement 66 includes a vertical vapor generation stack 68 including suitable heaters, represented at 70, in communication with the duct 18 at an opening 72. A duct 74 communicates between the duct 18 upstream of the opening 72 and an inlet air dispenser 76 at the top of the stack 68 just below a vaporizing nozzle 78, which may be an ultrasonic nozzle, into which a 35% solution of hydrogen peroxide is fed. The resultant saturated air, hydrogen peroxide solution, and water mixture flows through the opening 72 into the duct 18 and into and through a heat exchanger 80. The function of the heat exchanger is to condense excess water out of the airstream and to maintain a desired processing temperature of, say, 200° F. As in FIG. 1, the duct 18 leads to the vapor delivery inlet manifold 30 as before.

Referring now to FIG. 3, a pre-heat intake manifold 82 is mounted adjacent the inlet side of the inlet iso-box 40. The manifold 82 covers five indexing stations 84 in a chamber 86. A duct 88 communicates between the manifold 82 and the duct 54 (FIG. 1) to transmit heated air to the reservoir 82. An exhaust manifold 90 below the chamber 86 communicates with an exhaust duct 92.

Referring now to FIG. 4, a condensation unit 94 for one station is mounted between the inlet iso-box 40 (FIG. 1) and the vapor delivery inlet manifold 30 (shown beneath the chamber 34, rather than above as in FIG. 1). While the duct 18 communicates with the top end of the condensation unit 94, the bottom end of the latter communicates via a duct 96 with the inlet to the vapor delivery inlet manifold 30. A branch duct 98 communicates between the duct 18 and the return duct 44 (FIG. 1). A further branch duct 100 communicates between the branch duct 98 and the duct 96.

Referring now to FIG. 5, a spray unit 102 is mounted in front of the condensation unit 94 in the space of one indexing station for spraying liquid hydrogen peroxide into each container 38 as it indexes therebelow. An exhaust outlet 104 is mounted beneath the station.

INDUSTRIAL APPLICABILITY

It should be apparent that the two basic embodiments of the invention serve to provide a closed loop container sterilization system and associated drying section which are adaptable to a conventional forming, filling and sealing machine wherein a predetermined number of stations, say, fourteen, are provided within a suitable cooperating tunnel or chamber, between the bottom forming and the top filling and forming stations.

While but two basic and three supplementary embodiments of the invention are disclosed, other modifications within the scope of the following claims are possible.

The embodiments of the invention in which an exclusive property or privilege is claimed are defined as follows:

1. A sterilization system for containers being conveyed via a conveyor, said system comprising a closed loop of ductwork interconnecting in series a blower for blowing sterile air into said ductwork and for directing through said closed loop a flow of a mixture of air, vaporized hydrogen peroxide, and vaporized water; a duct heater mounted in the ductwork to raise the temperature of the sterile air to a predetermined minimum temperature; one of a vapor generation pool or a vapor generation stack with heater means operatively connected thereto, said vapor generation pool or stack providing a vaporized hydrogen peroxide solution into said ductwork; a vapor delivery inlet manifold and vapor delivery return manifold, a chamber intermediate said vapor delivery inlet manifold and said vapor delivery return manifold adapted to having said conveyor move laterally therethrough and having said mixture flow across the chamber from said vapor deliver inlet manifold to said vapor delivery return manifold, and said ductwork continuing from said vapor delivery return manifold back to said blower.

2. The sterilization system described in claim 1, further comprising a drying air inlet and exhaust manifold adjacent the exit of said vapor delivery inlet manifold, a second blower, external said closed loop, and a duct including a filter and a heater communicating between said blower and said drying air inlet manifold.

3. The sterilization system described in claim 2, further comprising a first iso-box mounted at the inlet to said vapor delivery inlet manifold, and a second iso-box mounted intermediate said vapor delivery inlet manifold and said drying air inlet manifold.

4. The sterilization system described in claim 3, further comprising a pre-heat intake manifold and an exhaust manifold adjacent the upstream end of said first iso-box and said vapor delivery inlet manifold, and a duct communicating between said preheat intake manifold and said duct between said second blower and said drying air inlet manifold.

5. The sterilization system described in claim 3, further comprising a condensation unit mounted intermediate said first iso-box and said vapor deliver inlet manifold, and duct means communicating between said condensation unit and each of said vapor delivery inlet and return manifolds.

6. The sterilization system described in claim 5, further comprising a spray unit mounted intermediate said first iso-box and said condensation unit for spraying liquid hydrogen peroxide into said container.

7. The sterilization system described in claim 2, wherein said containers are indexed through a plurality of stations past said vapor delivery inlet manifold and said drying air inlet manifold.

8. The sterilization system described in claim 7, wherein the number of stations is fourteen.

9. The sterilization system described in claim 1, wherein said one of a vapor generation pool and a vapor generation stack is a vapor generation stack and wherein said vapor generation stack includes a vertical stack of heaters adjacent an opening into said ductwork, an inlet at the top thereof for receiving a 35% solution of hydrogen peroxide, an inlet air dispenser adjacent the top inlet, and a duct communicating between said inlet air dispenser and said ductwork intermediate said opening and said duct heater.

10. The sterilization system described in claim 9, wherein said heater means is a heat exchanger in said ductwork intermediate said opening and said vapor delivery inlet manifold.

11. The sterilization system described in claim 1, wherein said heater means includes a plurality of electric heaters mounted on said vapor generation pool, and an inlet into said vapor generation pool for admitting additional hydrogen peroxide when required.

12. A sterilization system for containers, said system comprising a closed loop of ductwork interconnecting in series a blower for blowing sterile air into and directing through said closed loop a flow of a hydrogen peroxide sterilant, a duct heater for raising the temperature of said sterile air to a predetermined temperature, a vapor generation pool containing a hydrogen peroxide solution, at least one electric heater operatively connected to said vapor generation pool to maintain said solution at a predetermined temperature, a vapor delivery inlet manifold, a vapor delivery return manifold, a chamber intermediate the vapor delivery inlet manifold and the vapor delivery return manifold adapted to having a conveyor move therethrough bearing said containers to be sterilized by said flow of said hydrogen peroxide sterilant, said ductwork continuing back to said blower, and a drying air inlet manifold and a drying air exhaust manifold adjacent the exit of said vapor delivery inlet and return manifolds, a chamber intermediate the drying air inlet manifold and drying air exhaust manifold adapted to having said conveyor move therethrough to accommodate the remove of the sterilant from the containers, a duct communicating between said drying air inlet manifold and a second blower, said second blower adapted to blowing air into said drying air inlet manifold across said containers to said drying air exhaust manifold, and a duct heater operatively mounted in said duct for heating said air from said second blower.

13. A sterilization system for containers, said system comprising a closed loop of ductwork interconnecting in series a blower for blowing air into and directing through said closed loop a flow of hydrogen peroxide sterilant, a duct heater for raising the temperature of said sterile air to a predetermined temperature, a vapor generation stack including at least one heater and a vaporizing nozzle and having an air dispenser operatively connected thereto, a heat exchanger for condensing excess water out of the sterilant flow and to maintain a predetermined temperature, a vapor delivery inlet manifold, a vapor delivery return manifold, a chamber intermediate the vapor delivery inlet manifold and the vapor delivery return manifold adapted to having a conveyor move therethrough bearing said containers to be sterilized by said flow of said hydrogen peroxide sterilant, said ductwork continuing from said vapor delivery return manifold directly back to said blower, and a drying air inlet manifold and a drying air exhaust manifold adjacent the exit end of said vapor delivery inlet and return manifolds, a chamber intermediate the drying air inlet manifold and the drying air exhaust manifold adapted to having said conveyor move therethrough to accommodate the removal of the sterilant from the containers, a duct communicating between said drying air inlet manifold and a second blower, said second blower adapted to blowing air into and across said drying air inlet manifold, and a duct heater operatively mounted in said duct for heating said air from said second blower.

14. The sterilization system described in claims 12 or 13, and a first iso-box mounted at the entrance to said vapor delivery inlet manifold, and a second iso-box mounted intermediate said vapor delivery inlet manifold and said drying air inlet manifold.

15. The sterilization system described in claim 14, and a pre-heat intake manifold, a pre-heat exhaust manifold and intermediate chamber aligned with said previously described chamber, immediately upstream of said first iso-box, and a duct communicating between said pre-heat intake manifold and said duct between said drying air inlet manifold and said second blower.

16. The sterilization system described in claims 12 or 13, wherein said conveyor indexes a predetermined number of times while traversing through said chamber.

17. The sterilization system described in claim 16, wherein said number of indexes is on the order of fourteen.

18. The sterilization system described in claim 16, and a condensation station having an inlet end and an outlet end mounted intermediate said first iso-box and said vapor return manifold, a first branch duct communicating between said inlet end and said closed loop of ductwork, a second branch duct communicating between said outlet end and said vapor delivery inlet manifold.

19. The sterilization system described in claim 18, and a spray station mounted intermediate said condensation station and said first iso-box.

20. The sterilization system described in claims 12 or 13, wherein said hydrogen peroxide sterilant consists of a mixture of air, vaporized hydrogen peroxide, and vaporized water.

21. The sterilization system described in claims 12 or 13, wherein said ductwork is insulated with an interior coating of inert material.

22. The sterilization system described in claim 21, wherein said inert material is Teflon.

* * * * *